US009714220B2

(12) United States Patent
Tsai et al.

(10) Patent No.: US 9,714,220 B2
(45) Date of Patent: Jul. 25, 2017

(54) TETRADENTATE ORGANIC LIGAND H₃-MN-16BN CONTAINING LONG ALKYL GROUP, PRECURSOR THEREOF, AND METHOD FOR PREPARING THE SAME

(71) Applicant: INSTITUTE OF NUCLEAR ENERGY RESEARCH, ATOMIC ENERGY COUNCIL, EXECUTIVE YUAN, R.O.C., Taoyuan (TW)

(72) Inventors: Jia-Dong Tsai, Taoyuan (TW); Yu Chang, Taoyuan (TW); Kuei-Lin Lu, Taoyuan (TW); Cheng-Fang Hsu, Taoyuan (TW)

(73) Assignee: Institute of Nuclear Energy Research, Atomic Energy Council, Executive Yuan, R.O.C., Taoyuan (TW)

( * ) Notice: Subject to any disclaimer, the term of this patent is extended or adjusted under 35 U.S.C. 154(b) by 0 days.

(21) Appl. No.: 14/921,070

(22) Filed: Oct. 23, 2015

(65) Prior Publication Data
US 2017/0114009 A1   Apr. 27, 2017

(51) Int. Cl.
*C07C 323/25* (2006.01)
*C07C 319/02* (2006.01)
*C07C 67/08* (2006.01)
*C07C 69/24* (2006.01)

(52) U.S. Cl.
CPC ............ *C07C 323/25* (2013.01); *C07C 67/08* (2013.01); *C07C 69/24* (2013.01); *C07C 319/02* (2013.01)

(58) Field of Classification Search
CPC ..... C07C 323/25; C07C 319/02; C07C 319/20; C07C 67/08; C07C 69/24
See application file for complete search history.

(56) References Cited

U.S. PATENT DOCUMENTS 8,329,879 B2*  12/2012  Liu ................. C07C 323/41
                                                        534/10
2015/0322005 A1*  11/2015  Liu ..................... C07F 13/00
                                                        534/14

OTHER PUBLICATIONS

Tang, I., et al., Synthesis and applications of 188Re-MN-16ET/Lipiodol in hepatocellular carcinoma animal model, 2011, Nuclear Medicine and Biology, vol. 38, pp. 1043-1052.*
Tang, I-Chang, et al., Synthesis and application of Re-MN-16ET/Lipiodol in a hepatocellular carcinoma animal model, 2011, Nuclear Medicine and Biology, vol. 38, pp. 1043-1052.*

* cited by examiner

*Primary Examiner* — Yate K Cutliff
(74) *Attorney, Agent, or Firm* — Rosenberg, Klein & Lee

(57) ABSTRACT

A tetradentate organic ligand H₃-MN-16Bn containing a long alkyl group, a precursor thereof, and a method for preparing the same are revealed. A precursor of H₃-MN-16Bn, benzyl 16-bromohexadecanate, is obtained by esterification reaction of 16-bromohexadecanoic acid. Then bimolecular nucleophilic substitution reaction ($S_N2$) of Benzyl 16-bromohexadecanate with nitrogen sulfide ($N_2S_2$) is carried out to get H₃-MN-16Bn that is used as a standard hydrolysis metabolites of non-radioactive $^{185}$Re-complex compound.

10 Claims, 2 Drawing Sheets

TETRADENTATE ORGANIC LIGAND H₃-MN-16BN CONTAINING LONG ALKYL GROUP, PRECURSOR THEREOF, AND METHOD FOR PREPARING THE SAME

FIELD OF THE INVENTION

The present invention relates to a compound and a method for preparing the same, especially to a tetradentate organic ligand H$_3$-MN-16Bn containing a long alkyl group, a precursor thereof and a method for preparing the same.

BACKGROUND OF THE INVENTION

Liver is the organ that plays a major role in metabolism of human body and contains a series of enzymes as catalysts for drug oxidation, reduction and hydrolysis. At the same time, there are some other enzymes used for catalyzing the synthesis reaction of drugs with certain substances. The compound formed by drug molecules and substances combined will be excreted in urine or feces. According to the above metabolic pathway, drug metabolism can be defined as structural changes of a drug catalyzed by enzymes. After being taken into the body, almost every drug is going to be metabolized at certain degrees. The metabolites of the drug may have no activity or have similar activity as the original drug. Thus the metabolites continue to work to have therapeutic effect or toxicity.

Recently, there is a potential drug for treatment of liver cancer-$^{188}$ReO-MN-16ET. A ligand H$_3$-MN-16ET is reacted and labeled with radioactive $^{188}$Re to create $^{188}$ReO-MN-16ET. Then $^{188}$ReO-MN-16ET is dissolved in Lipiodol to form $^{188}$ReO-MN-16ET/Lipiodol, a diagnostic and therapeutic radiopharmaceutical for liver cancers. In order to learn hydrolysis metabolites of $^{188}$ReO-MN-16ET in rats, researchers have tried to synthesize the hydrolysis metabolite [N-(2-Thioethyl)-3-aza-19-carboxylic acid-3-(2-thioethyl)octadecanamdo]oxorhenium(V) (ReO-MN-16COOH). During the synthesis process, ReO-MN-16ET can be used as starting material and hydrolysis occurs when an acid or a base is used as a catalyst so as to get ReO-MN-16COOH theoretically. However, no reaction occurs under acid catalysis in practice and the product obtained under base catalysis contains no ReO-MN-16COOH. The results are not as expected. Thus there is a need to find out other compound able to create ReO-MN-16COOH after hydrolysis. The compound can be used as a standard of hydrolysis metabolites of non-radioactive $^{185}$Re-complex compound.

SUMMARY

Therefore it is a primary object of the present invention to provide a tetradentate organic ligand H$_3$-MN-16Bn containing a long alkyl group, a precursor thereof, and a method for preparing the same. A new compound-H$_3$-MN-16Bn with novel structural formula and a method for preparing the same have been developed.

It is another object of the present invention to provide a tetradentate organic ligand H$_3$-MN-16Bn containing a long alkyl group, a precursor thereof, and a method for preparing the same. H$_3$-MN-16Bn can be used as a standard of hydrolysis metabolites of non-radioactive $^{185}$Re-complex compound. The precursor means those used during manufacturing process of H$_3$-MN-16Bn.

In order to achieve the above objects, a tetradentate organic ligand H$_3$-MN-16Bn containing a long alkyl group of the present invention has the following structural formula.

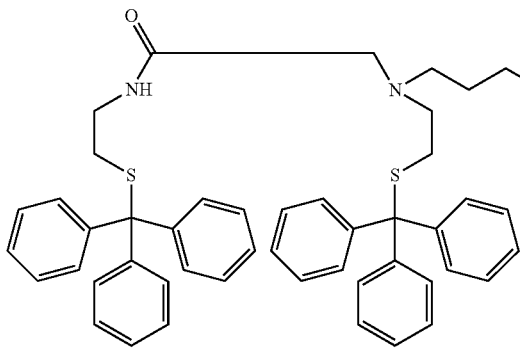

A method for preparing the tetradentate organic ligand H$_3$-MN-16Bn includes the following steps. First dissolve 16-bromohexadecanoic acid and thionyl chloride in a first solvent to get a first solution. Then heat the first solution under reflux, cool the first solution, and concentrate the first solution by removing the excess thionyl chloride and the excess first solution to form a second solution. Add phenylmethanol into the second solution to form benzyl 16-bromohexadecanate in a solid form. Next mix the benzyl 16-bromohexadecanate, nitrogen sulfide (N$_2$S$_2$), a dehydrogenating agent, a molecular sieve and a second solvent to form a third solution. Then heat the third solution under reflux. Lastly filter the third solution to get a crude product and purify the crude product to get the tetradentate organic ligand H$_3$-MN-16Bn containing a long alkyl group.

Benzyl 16-bromohexadecanate mentioned above is a precursor of the tetradentate organic ligand H$_3$-MN-16Bn containing a long alkyl group which has the following structural formula:

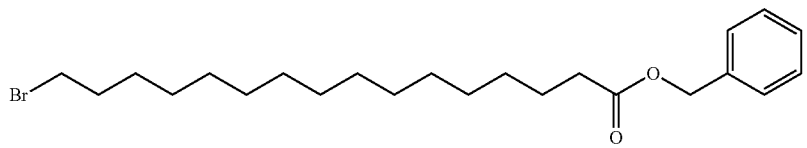 [SMILES: O=C(CCCCCCCCCCCCCCCBr)OCc1ccccc1]

DETAILED DESCRIPTION

In order to make the structure and characteristics as well as the effectiveness of the present invention to be further understood and recognized, the detailed description of the present invention is provided as follows along with embodiments and accompanying figures.

Figure 1:
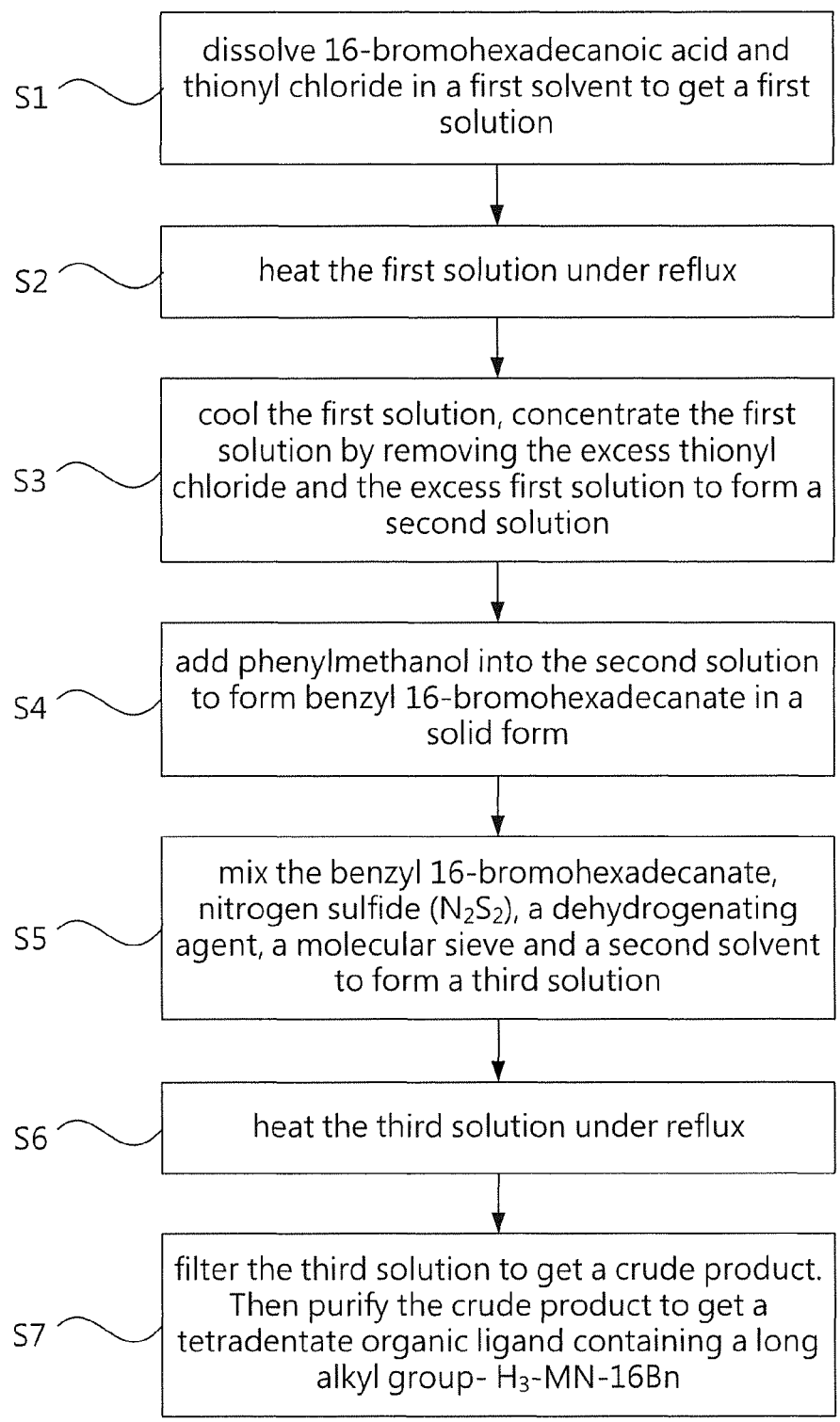
FIG. 1 is a flow chart showing steps of an embodiment of a method for synthesis of a tetradentate organic ligand $H_3$-MN-16Bn containing a long alkyl group according to the present invention.

Refer to FIG. 1, a method for preparing a tetradentate organic ligand-$H_3$-MN-16Bn according to the present invention includes the following steps.

Step S1: dissolve 16-bromohexadecanoic acid and thionyl chloride in a first solvent to get a first solution;

Step S2: heat the first solution under reflux;

Step S3: cool the first solution, concentrate the first solution by removing the excess thionyl chloride and the excess first solution to form a second solution;

Step S4: add phenylmethanol into the second solution to form benzyl 16-bromohexadecanate in a solid form;

Step S5: mix the benzyl 16-bromohexadecanate, nitrogen sulfide ($N_2S_2$), a dehydrogenating agent, a molecular sieve and a second solvent to form a third solution;

Step S6: heat the third solution under reflux; and

Step S7: filter the third solution to get a crude product. Then purify the crude product to get a tetradentate organic ligand containing a long alkyl group-$H_3$-MN-16Bn.

In order to synthesize the tetradentate organic ligand $H_3$-MN-16Bn containing a long alkyl group, the synthesis of a precursor of $H_3$-MN-16Bn is shown in the following equation 1.

Then the precursor is used for synthesis of the tetradentate organic ligand $H_3$-MN-16Bn containing a long alkyl group, as shown in the following equation 2.

(Equation 2)

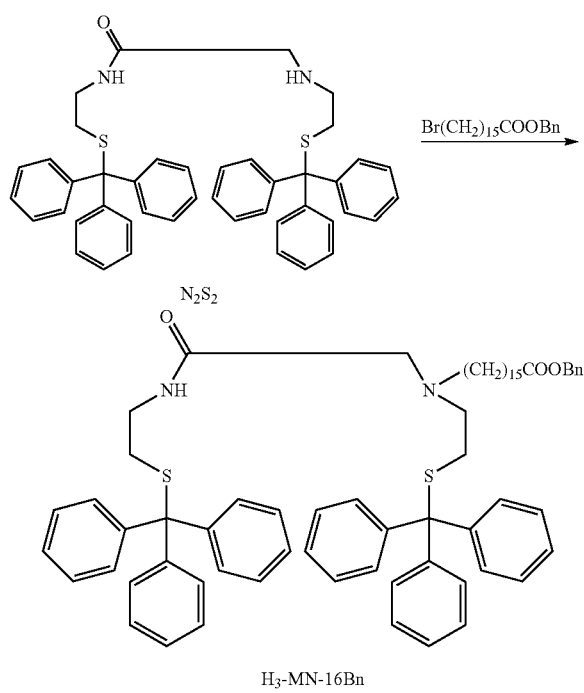

Figure 2:
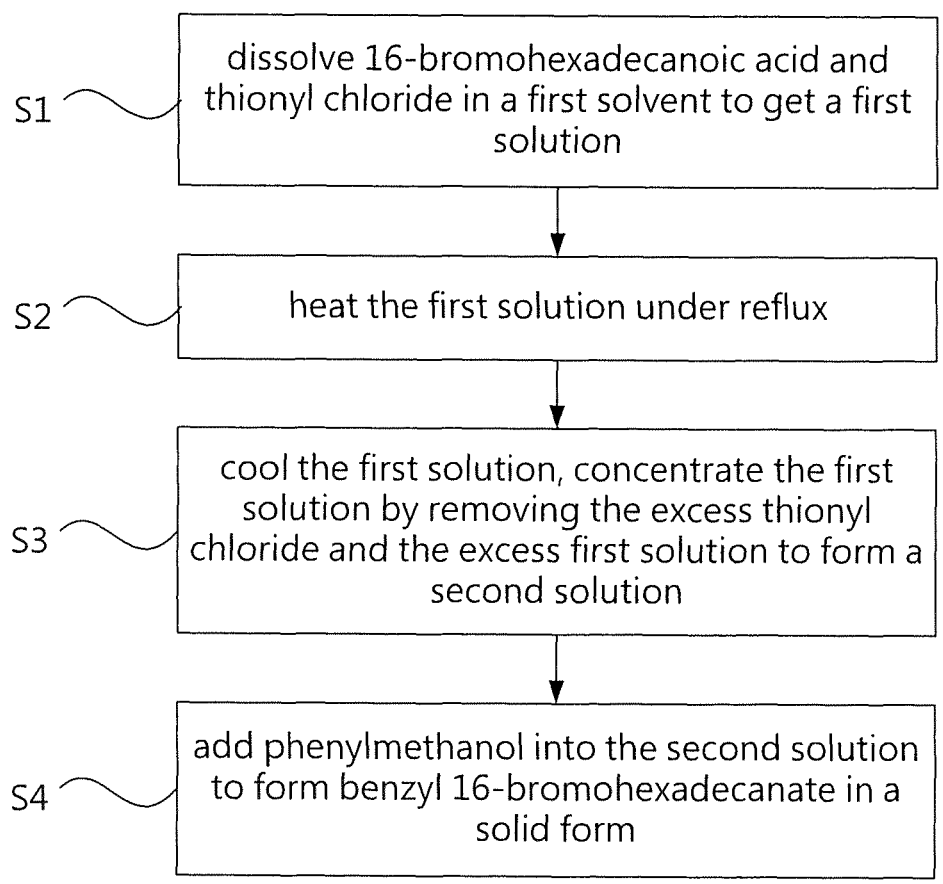
FIG. 2 is a flow chart showing steps of an embodiment of a method for synthesis of a precursor of a tetradentate organic ligand $H_3$-MN-16Bn containing a long alkyl group according to the present invention.

Refer to FIG. 2, the precursor of $H_3$-MN-16Bn, benzyl 16-bromohexadecanate, is obtained by esterification reaction of 16-bromohexadecanoic acid as shown in the steps S1 to S4 mentioned above. The flow chart including step S1 to step S7 shows how $H_3$-MN-16Bn is synthesized. Then bimolecular nucleophilic substitution ($S_N2$) reaction of ben- (Equation 1)

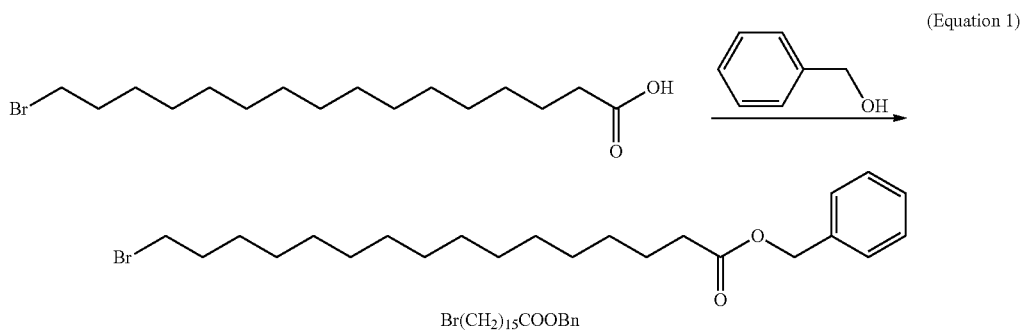

Br(CH$_2$)$_{15}$COOBn zyl 16-bromohexadecanate with nitrogen sulfide (N₂S₂) occurs to get the final product-H₃-MN-16Bn. The preparation method of the present invention features on simplicity of the processes and convenience of post treatment process.

During the manufacturing processes, benzyl 16-bromohexadecanate should be purified. The residual benzyl alcohol of the previous step should be removed in advance during purification. Water is used as a solvent for purification. Benzyl alcohol is slightly soluble in water while 16-bromohexadecanate is insoluble in water. Thus 16-bromohexadecanate is obtained easily by crystallization from the water, filtration and drying. No chromatography column is required and only water is used for purification. Water is easy to get and the used water can be recycled. The process is consistent with the principles of green chemistry.

Moreover, the dehydrogenation of secondary amine of the nitrogen sulfide (N₂S₂) is carried out first so that bimolecular nucleophilic substitution ($S_N2$) reaction of benzyl 16-bromohexadecanate with nitrogen sulfide (N₂S₂) can occur. A strong base-potassium hydroxide (KOH) is added as a dehydrogenating agent. KOH will not react with benzyl 16-bromohexadecanate so that there is no other secondary product derived and KOH has no effect on manufacturing processes. After completion of the reaction, the gross product is purified by column chromatography to get the final product H₃-MN-16Bn.

The first solvent in the step S1 is hexane while the second solvent in the step S5 is acetonitrile. In the step of heating the first solution under reflux, the solution is heated to reflux at 75~85° C. for 2 hours. In the step of heating the third solution under reflux, the third solution is heated under reflux at 80~90° C. for 48 hours. In the step S3 for forming a second solution, the solution is cooled to 50~60° C. and then is concentrated by vacuum evaporation for 3 hours. In the step of adding phenylmethanol into the second solution, the solution is stirred at room temperature for 16 hours and then repeat steps of adding water and stirring for 30 minutes, leaving the solution for 5 minutes, and removing the upper layer for at least 10 times. A lot of water is used to remove residual phenylmethanol.

According to the above steps, benzyl 16-bromohexadecanate and nitrogen sulfide are reacted under simple and easy reaction conditions. Then the product of H₃-MN-16Bn is obtained by a simple separation and purification way. The yield rate of the product is over 10%. The following use of the product is to get a carboxylate ion by hydrogenation or hydrolysis of the ester group at the rear end. The final product generated is ReO-MN-16COOH. This is a better way to produce hydrolysis metabolites of [188]ReO-MN-16ET in rats. This helps research development and a breakthrough in experiments.

The followings are data obtained by running the above steps and analytic results obtained by infrared spectroscopy and nuclear magnetic resonance spectroscopy.

[Synthesis of Benzyl 16-Bromohexadecanate]

Take and dissolve 5.0 g (14.9 mmol) 16-bromohexadecanoic acid in 30 mL hexane (used as solvent) and add 30 mL (413 mmol) thionyl chloride in a first solvent into the solution. Then heat under reflux at 80° C. for 2 hours. Cool the solution to 55° C. and remove excess thionyl chloride and hexane by vacuum evaporation for 3 hours. Next add 30 mL phenylmethanol already dehydrated by molecular sieve into the concentrated solution and stir the mixture at room temperature for 16 hours. Then add 300 mL water (10 times than the volume of phenylmethanol) and stir vigorously at room temperature for 30 minutes. Leave the solution for 5 minutes to separate two phases and remove the upper layer. Then add 300 mL water and stir vigorously for 30 minutes again. Repeat the steps 10 times for removing residual phenylmethanol by a lot of water and white solid is deposited from the solution. The solid product of Benzyl 16-bromohexadecanate (5.80 g, 91%) is obtained after vacuum filtration, washing with water and drying.

Analytical data for Benzyl 16-bromohexadecanate: $^1$H-NMR (300 MHz, CDCl₃): δ 7.35 (m, 5H, Ph), 5.11 (s, 2H, C17H₂), 3.40 (t, 2H, J=6.9 Hz, C1H₂), 2.35 (t, 2H, J=7.5 Hz, C15H₂), 1.85 (quint, 2H, J=7.8 Hz, C2H₂), 1.64 (m, 2H, C14H₂), 1.42 (m, 2H, C3H₂), 1.25 (m, 20H, C4H₂, C5H₂, C6H₂, C7H₂, C8H₂, C9H₂, C10H₂, C11H₂, C12H₂, C13H₂). $^{13}$C NMR (75 MHz, CDCl₃) δ 174.38 (C16), 136.82, 129.21 & 128.83 (Ph), 66.72 (C17), 35.02, 34.73, 33.52, 30.29, 30.24, 30.21, 30.12, 29.92, 29.80, 29.45, 28.86, & 25.63 (CH₂).

The structural formula is:

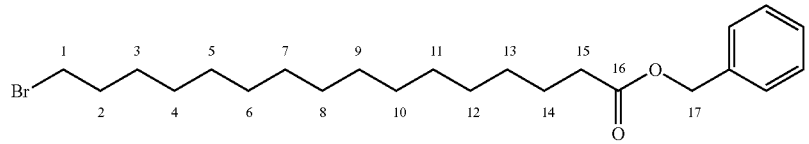 [SMILES: O=C(CCCCCCCCCCCCCCCBr)OCc1ccccc1]

Synthesis of (N-[2-((Triphenylmethyl)thio)ethyl]3-aza-18-benzyloxycarbonyl-3-[2-((triphenyl-methyl)thio)ethyl]octadecanamide) (H₃-MN-16Bn)

Take and dissolve 5.80 g (13.7 mmol) benzyl 16-bromohexadecanate, 14.0 g (20.5 mmol) nitrogen sulfide (N₂S₂), 1.54 g (27.4 mmol) potassium hydroxide (KOH), and 4 g molecular sieve in 107 mL acetonitrile (solvent) to form a solution. Then heat the solution under reflux at 85° C. for 48 hours. Filter the solution while it is still hot and get the filtrate. Gross product is obtained after vacuum evaporation of the filtrate. Then the gross product is separated and purified by column chromatography (ethyl acetate:hexane:dichloromethane=1:7:2) to get pale yellow oily product—2.41 g H₃-MN-16Bn (26%).

Analytical data for H₃-MN-16Bn: $^1$H-NMR (300 MHz, CDCl₃): δ 7.45 (m, 1H, NH), 7.41-7.14 (m, 35H, Ph), 5.11 (s, 2H, C25H₂), 3.01 (q, 2H, J=6.6 Hz, C3H₂), 2.83 (s, 2H, C5H₂), 2.37 (m, 6H, C2H₂, C6H₂ and C7H₂), 2.25 (m, 4H, C9H₂ &C23H₂), 1.64 (m, 4H, C10H₂ & C22H₂), 1.24 (m, 22H, C11H₂, C12H₂, C13H₂, C14H₂, C15H₂, C16H₂, C17H₂, C18H₂, C19H₂, C20H₂ & C21H₂). $^{13}$C NMR (75 MHz, CDCl₃): δ 174.34 (C24O), 171.97 (C4O), 145.43, 136.79, 131.12, 131.04, 130.35, 130.05, 129.68, 129.40, 129.29, 128.86, 128.74, 128.56, 128.52, 128.22, 127.71, 127.41, 127.23 & 126.46 (Ph), 67.39 (C25), 66.70 (C1 & C8), 58.91, 55.52, 54.48, 38.57, 34.99, 32.63, 30.66, 30.32, 30.18, 29.91, 29.79, 27.97, 27.73 & 25.60 (CH₂).

The structural formula is:

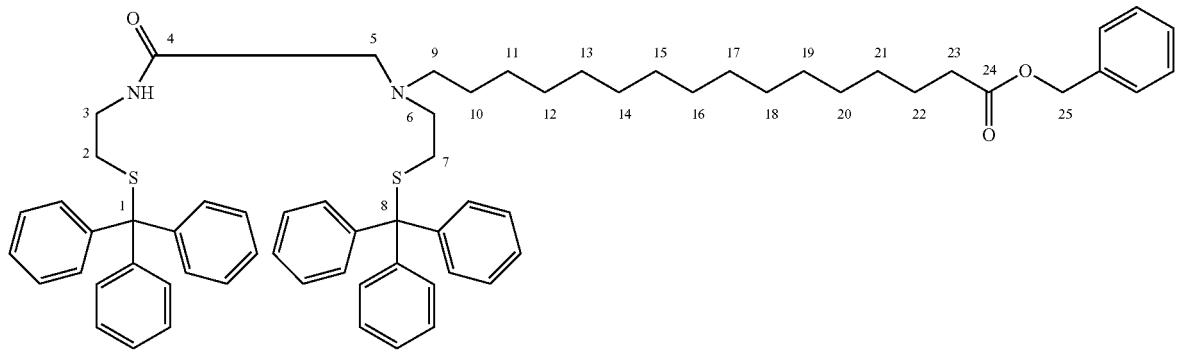 [SMILES: O=C(CN(CCCCCCCCCCCCCCCC(=O)OCc1ccccc1)CCSC(c1ccccc1)(c1ccccc1)c1ccccc1)NCCSC(c1ccccc1)(c1ccccc1)c1ccccc1]

In summary, the tetradentate organic ligand H3-MN-16Bn containing the long alkyl group, a precursor thereof, and the method for preparing the same of the present invention feature on that the manufacturing steps are not complicated. The carboxylate ion is obtained easily and conveniently by hydrogenation or hydrolysis of the ester group at the rear end and the final product generated is ReO-MN-16COOH that the research needs. The present invention provides a novel compound and a method for preparing the same with usefulness and industrial value.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. A tetradentate organic ligand $H_3$-MN-16Bn containing a long alkyl group is represented by the following structural formula:

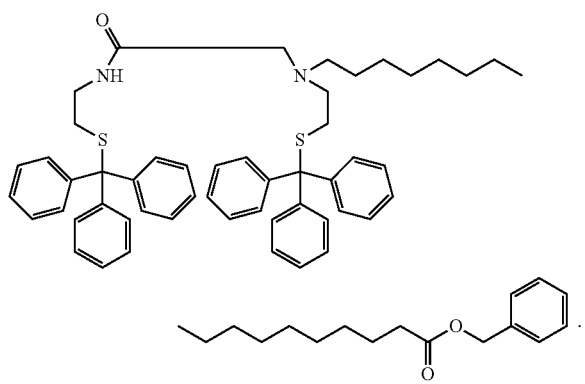

2. A method for preparing a tetradentate organic ligand $H_3$-MN-16Bn containing a long alkyl group comprising the steps of:

dissolving 16-bromohexadecanoic acid and thionyl chloride in a first solvent to get a first solution;
heating the first solution under reflux;
cooling the first solution, and concentrating the first solution by removing excess thionyl chloride and excess first solution to form a second solution;
adding phenylmethanol into the second solution to form benzyl 16-bromohexadecanate in a solid form;
mixing the benzyl 16-bromohexadecanate, nitrogen sulfide ($N_2S_2$), a dehydrogenating agent, a molecular sieve and a second solvent to form a third solution;
heating the third solution under reflux; and
filtering the third solution to get a crude product and then purifying the crude product to get the tetradentate organic ligand $H_3$-MN-16Bn containing a long alkyl group.

3. The method as claimed in claim 2, wherein the first solvent is hexane.

4. The method as claimed in claim 2, wherein the second solvent is acetonitrile.

5. The method as claimed in claim 2, wherein the first solution is heated under reflux at 75~85° C. for 2 hours in the step of heating the first solution under reflux.

6. The method as claimed in claim 2, wherein the third solution is heated under reflux at 80~90° C. for 48 hours in the step of heating the third solution under reflux.

7. The method as claimed in claim 2, wherein the dehydrogenating agent is potassium hydroxide (KOH).

8. The method as claimed in claim 2, wherein a gross product is separated and purified by column chromatography in the step of purifying the crude product.

9. The method as claimed in claim 2, wherein the first solution is cooled to 50~60° C. and concentrated by vacuum evaporation for 3 hours in the step of forming a second solution.

10. The method as claimed in claim 2, wherein the second solution is stirred at room temperature for 16 hours in the step of adding phenylmethanol and the step of adding phenylmethanol further includes the steps of:
adding water and stirring for 30 minutes;
leaving mixture for 5 minutes, and
removing an upper layer;
wherein the above three steps are repeated for at least ten times.

* * * * *